United States Patent
Holmes et al.

(10) Patent No.: US 8,478,842 B2
(45) Date of Patent: Jul. 2, 2013

(54) DATA COMMUNICATION IN A PICTURE ARCHIVING AND COMMUNICATIONS SYSTEM NETWORK

(75) Inventors: Colin J. Holmes, Vancouver, WA (US); Derek Scherger, Calgary (CA); Michael Beauregard, Calgary (CA); Glen Lehmann, Crossfield (CA); Pierre Lemire, Calgary (CA)

(73) Assignee: Calgary Scientific Inc. (CA)

( * ) Notice: Subject to any disclaimer, the term of this patent is extended or adjusted under 35 U.S.C. 154(b) by 85 days.

(21) Appl. No.: 12/592,465

(22) Filed: Nov. 25, 2009

(65) Prior Publication Data

US 2010/0146044 A1 Jun. 10, 2010

Related U.S. Application Data

(60) Provisional application No. 61/193,409, filed on Nov. 26, 2008.

(51) Int. Cl.
*G06F 15/16* (2006.01)

(52) U.S. Cl.
USPC ............ 709/219; 709/203; 709/217; 707/705

(58) Field of Classification Search
USPC .......... 707/705, 713, 731, 769, 770; 709/203, 709/217, 219
See application file for complete search history.

(56) References Cited

U.S. PATENT DOCUMENTS

| | | | |
|---|---|---|---|
| 7,650,198 B2 * | 1/2010 | Dorgelo et al. ............... | 700/108 |
| 7,870,153 B2 * | 1/2011 | Croft et al. .................... | 707/781 |
| 2007/0124410 A1 * | 5/2007 | Hofstetter ..................... | 709/217 |
| 2008/0052126 A1 * | 2/2008 | Sasai et al. ........................ | 705/3 |
| 2009/0164474 A1 * | 6/2009 | Noumeir ........................ | 707/10 |
| 2010/0005055 A1 * | 1/2010 | An et al. ............................. | 707/2 |
| 2010/0293164 A1 * | 11/2010 | Weese et al. .................. | 707/737 |
| 2010/0299517 A1 * | 11/2010 | Jukic et al. .................... | 713/150 |

OTHER PUBLICATIONS

Van Ooijen P.M.A. et al., Journal of Digital Imaging, Use of a Thin-Section Archive and Enterprise 3-Dimensional Software for Long-Term Storage of Thin-Slice CT Data Sets—A Reviewers' Response, vol. 0, No. 0, 2007, pp. 1-5.

Toland, Christopher et al., A Suggested Classification Guide for PACS Client Applications: The Five Degrees of Thickness, Department of Diagnostic Radiology, University of Maryland School of Medicine, Baltimore, MD, Published online: Oct. 4, 2006.

Meenan, Christopher et al., Journal of Digital Imaging, Use of a Thin-Section Archive and Enterprise 3D Software for Long-Term Storage of Thin-Slice CT Data Sets, Department of Diagnostic Radiology, University of Maryland School of Medicine, Baltimore, MD, Published online: Sep. 20, 2006.

* cited by examiner

*Primary Examiner* — Mohamed Ibrahim
(74) *Attorney, Agent, or Firm* — Meunier Carlin & Curfman, LLC

(57) ABSTRACT

A method and system for accessing a data file is provided. At a server computer a request for accessing a data file of a plurality of data files stored in a database is received. The server computer is connected to the database via a first communication link and a second communication link. Metadata associated with the data file in the database are accessed via the first communication link using a first query protocol. In dependence upon the metadata the data file is located in the database. At least a portion of data stored in the data file is then accessed in the database via the second communication link using a second query protocol.

15 Claims, 4 Drawing Sheets

DATA COMMUNICATION IN A PICTURE ARCHIVING AND COMMUNICATIONS SYSTEM NETWORK

This application claims the benefit of U.S. Provisional Patent Application No. 61/193,409 filed Nov. 26, 2008, the entire contents of which are incorporated herein by reference.

FIELD OF THE INVENTION

The instant invention relates to the storage, archiving, networking, and retrieval of medical imaging data and in particular to a method and system for enabling improved data communication in a Picture Archiving and Communications System (PACS) network.

BACKGROUND

Modern hospitals utilize medical images from a variety of imaging devices such as, for example, a Computer Tomography (CT) scanner or a Magnetic Resonance Imaging (MRI) scanner. The image data are then stored and transmitted using a computer network—typically comprising client-server architecture—to enable medical professionals to view and diagnose the captured medical images at a workstation conveniently placed, for example, in a medical professional's office.

Hospitals and diagnostic clinics typically use PACS systems to import, store and manipulate image data. PACS systems are computer networks dedicated to the storage, retrieval, distribution, and representation of medical image data. PACS is offered by virtually all the major medical imaging equipment manufacturers, medical IT companies, as well as many independent software companies. Basic PACS software is freely available on the Internet.

In order to facilitate communication of medical image data and associated information the Digital Imaging Communications in Medicine (DICOM) standard has been developed and is now commonly used for image data communication between medical devices which include PACS systems.

While the DICOM communication standard has enabled robust, standardized communication between medical devices it was originally conceived for the exchange of two dimensional pictures. DICOM systems suffer from significant overhead for transferring individual images which presents performance challenges. With the increase in resolution as well as the increased application of 3 and 4 dimensional imaging in present day medical imaging devices, the size of image data files and their number contained within an individual imaging study has increased substantially and, as result, the slow transmission of image data using the DICOM communications protocols creates a bottleneck in present day PACS systems. Within a single medical device it is frequently the practice to use non-DICOM high performance communications and file transfer protocols for the internal movement of these large imaging studies.

It is desirable to provide a method and system that provides high performance data transfer between medical devices while preserving the benefit of information sharing using an existing communication standard.

SUMMARY OF EMBODIMENTS OF THE INVENTION

In accordance with embodiments of the present invention there is provided a method for accessing data files. At a server computer a request for accessing a data file of a plurality of data files stored in a database is received. The server computer is connected to the database via a first communication link and a second communication link. Metadata associated with the data file in the database are accessed via the first communication link using a first query protocol. In dependence upon the metadata the data file is located in the database. At least a portion of data stored in the data file is then accessed in the database via the second communication link using a second query protocol.

In accordance with embodiments of the present invention there is further provided a storage medium having stored therein executable commands for execution on a processor of a server computer. The server computer is connected to the database via a first communication link and a second communication link. The processor when executing the commands accesses metadata associated with the data file in the database via the first communication link using a first query protocol. The processor then locates the data file in the database in dependence upon the metadata. After locating the data file the processor accesses at least a portion of data stored in the data file via the second communication link using a second query protocol.

BRIEF DESCRIPTION OF THE DRAWINGS

Exemplary embodiments of the invention will now be described in conjunction with the following drawings, in which.

DETAILED DESCRIPTION OF EMBODIMENTS OF THE INVENTION

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

While embodiments of the invention will be described for data communication in a PACS network for the sake of simplicity, it will become evident to those skilled in the art that the embodiments of the invention are not limited thereto, but are applicable in numerous other fields where constraining standards reduce performance while accessing large data files from client server computer networks.

Figure 1:
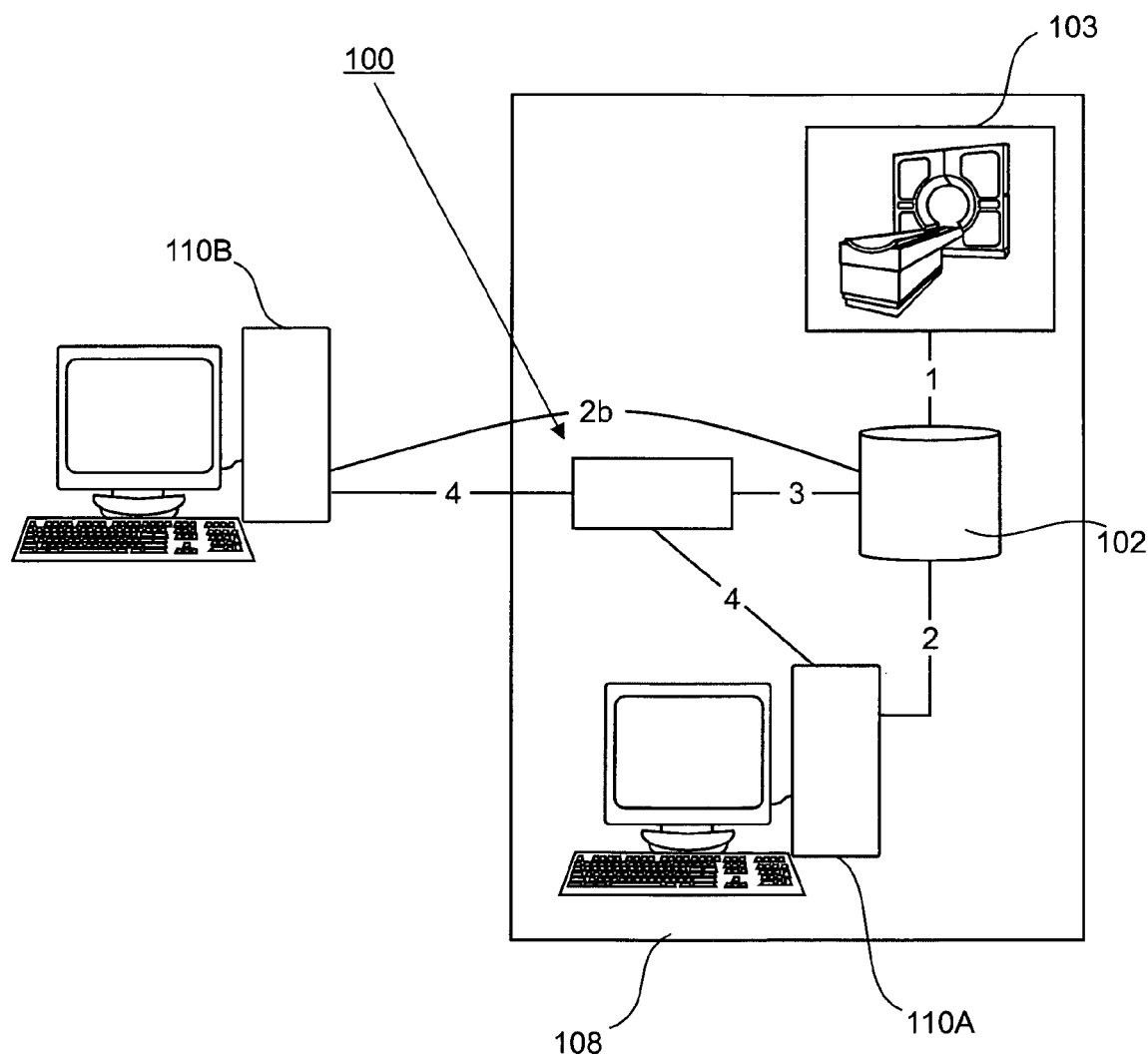
FIGS. 1 and 2 are simplified block diagrams of a system for accessing data files according to an embodiment of the invention; and, FIG. 3 is a simplified flow diagram of a method for accessing data files according to an embodiment of the invention.
Figure 2:
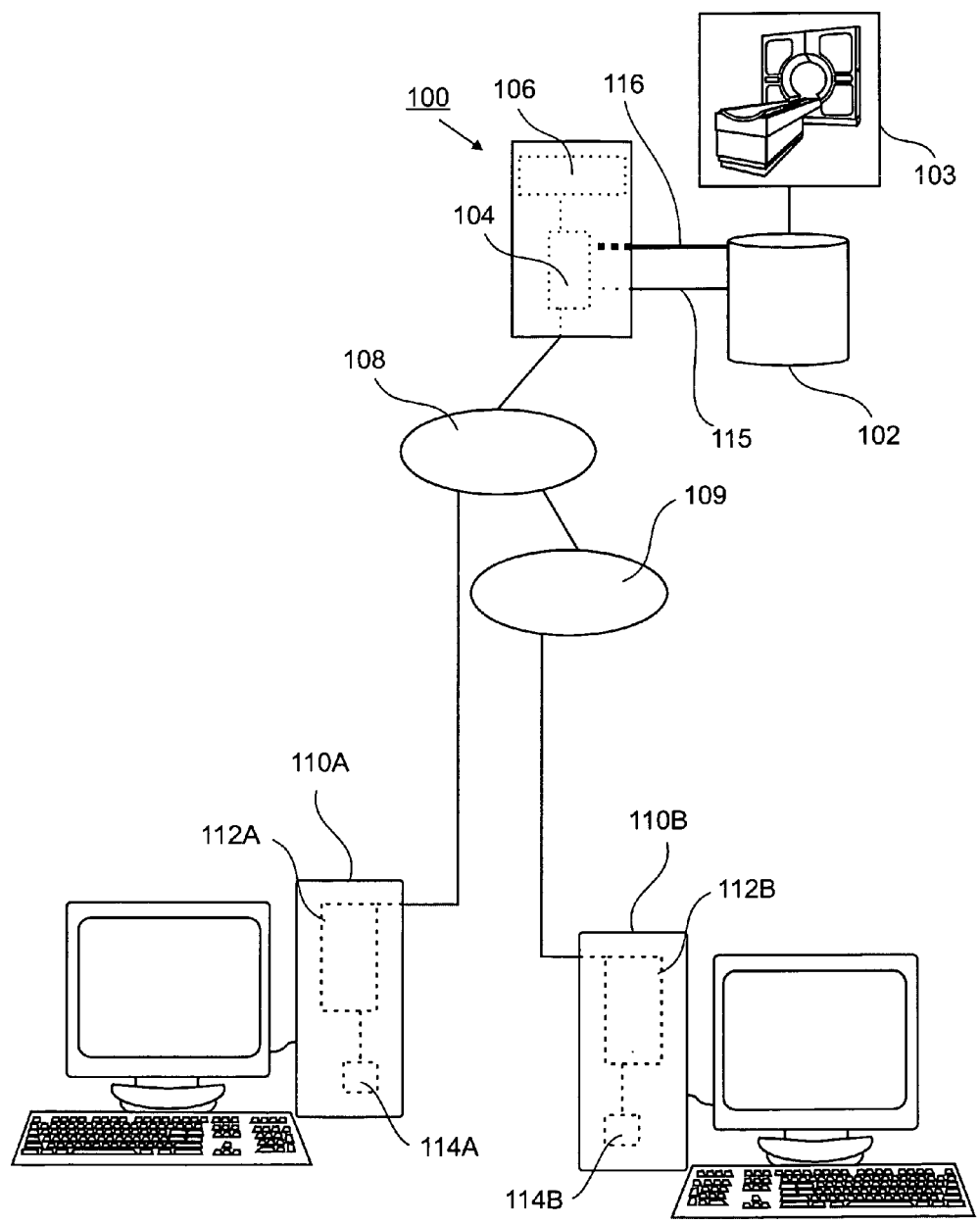

Referring to FIGS. 1 and 2, a system comprising a server computer 100 for implementing a method for accessing data files according to a preferred embodiment of the invention described herein below is shown. FIG. 1 illustrates the integration of the server computer 100 into an existing hospital network while FIG. 2 illustrates the implementation of the method for accessing data files in more detail with same reference numerals indicating same components.

As will become evident to those skilled in the art, the server computer 100 is not limited to imaging applications in a hospital setting as shown in FIGS. 1 and 2 but also implementable in various other applications where large data files are processed for generating display data for viewing. Image data acquired using a medical imaging device 103 such as, for example, a MRI imaging device, are transferred —1- to a PACS database 102.

Using existing PACS technology and software a data file stored in the PACS data base 102 is retrieved and transferred —2, 2b—from the data base to, for example, a diagnostic workstation 110A, 110B using the DICOM communications protocol where it is processed for viewing by a medical practitioner. The diagnostic workstation is connected to the PACS database 102, for example, via a Local Area Network (LAN) such as a hospital network —2—or remotely via, for example, a Wide Area Network (WAN) or the Internet —2b.

Using the method for accessing data files according to a preferred embodiment of the invention, the data file is processed using the server computer 100. Mouse and keyboard commands are sent —4- to the server computer 100, the image processing is performed in dependence upon the commands by the server computer 100, and view data indicative of the resulting images are sent back —4- to the diagnostic workstation for display. For performing the image processing the server computer 100 accesses —3—different types of data using different connections 115, 116 and using different communication protocols associated with the respective connections. Metadata are accessed according to a DICOM query protocol of the PACS database 102 and using the DICOM communications protocol on the normal hospital network 115 enabling information sharing using an existing communication standard, while image or large volume data are accessed using the high performance connection 116 together with a non-DICOM query protocol and a non-DICOM communication protocol.

In existing systems the server computer is interfaced with the PACS database using one or several of the DICOM query/retrieve or other transfer protocols. Using the DICOM transfer protocol the data file is transferred to the server computer from end-to-end resulting in significant transfer times. Even if the data file is stored locally the DICOM transfer protocol typically requires transferring of the data file using a local loopback interface. In the system using the method for accessing data files according to a preferred embodiment of the invention, however, the separation of DICOM communications over the standard network 115 from high performance data transfers over a dedicated high performance connection 116 obviates the need for data duplication—i.e. storage of the data file in memory of the server computer 100 for processing—and transfer of the data file between the PACS database 102 and the server computer 100 substantially increasing performance of the overall system.

Figure 3:
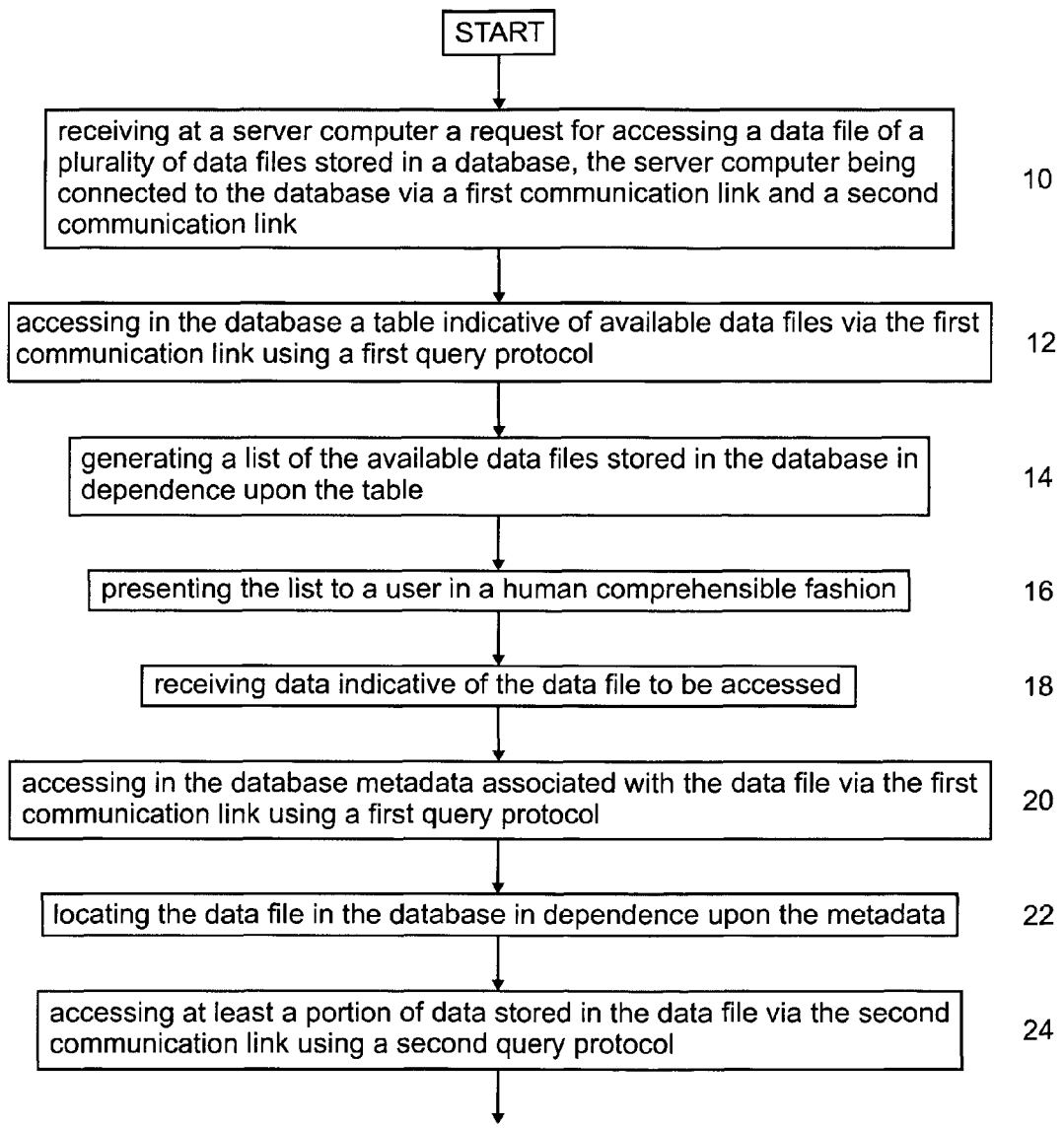
Figure 3:
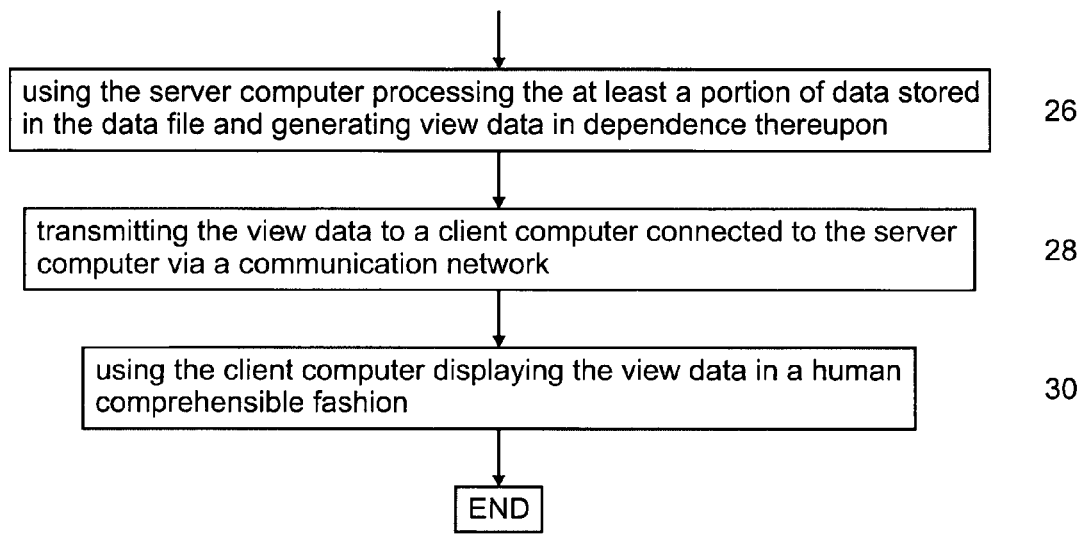

Referring to FIG. 3, a method for accessing data files according to the preferred embodiment of the invention is provided. The method is implemented using the system shown in FIGS. 1 and 2. A plurality of data files is stored in the database 102 such as, for example, a PACS database, and are accessible according to a query protocol of the database 102 other than the standard DICOM query protocol. The server computer 100 is connected to the database 102 via the first communication link 115 and the second communication link 116. The server computer 100 comprises an interface for accessing the data files according to the query protocol of the database 102. Client computers 110A, 110B such as, for example, diagnostic workstations, are connected to the server computer 100 via a communication network, for example, client computer 110A via a LAN 108 and client computer 110B via a WAN 109 such as the Internet. Each client computer comprises a processor 112A, 112B and memory 114A, 114B. At 10, a processor 104 of the server computer 100 receives from the processor 112A, 112B of one of the client computers 110A, 110B a request for accessing a data file of a plurality of data files stored in the database 102. The processor 104 of the server computer 100 then accesses —12—in the database 102 a table indicative of available data files via the first communication link 115 using a first query protocol, for example, the standard DICOM query protocol. The processor 104 of the server computer 100 then generates —14—a list of the available data files stored in the database 102 in dependence upon the table which is then presented —16—at one of the client computers 110A, 110B to a user in a human comprehensible fashion. Using a user interface connected to the one of the client computers 110A, 110B the user provides data indicative of the data file to be accessed —18. Alternatively, the steps 12 to 18 are omitted and the data file to be accessed is determined by the processor 104 of the server computer 100, for example, during execution of an application program which requires access to the data file. At 20, the processor 104 of the server computer 100 accesses—via the connection 115—the relevant descriptive data concerning the data file—the "metadata"—according to the first query protocol, for example, the standard DICOM query protocol, which it uses to locate the data file in the PACS database 102. The processor 104 then locates —22—the data file in the database 102 in dependence upon the metadata. After locating the data file, the processor 104 accesses —24—at least a portion of data stored in the data file via the second communication link 116—a high performance connection—using a second query protocol—a high performance query protocol. Using the processor 104 the at least a portion of data stored in the data file is processed —26- and view data are generated in dependence thereupon. At 28, the view data are transmitted to one of the client computers 110A, 110B and displayed —30—in a human comprehensible fashion. Alternatively, the steps 26 to 30 are omitted; for example, during execution of an application program access to the data file is required for determining data other than view data.

The method for accessing data files according to the preferred embodiment of the invention are performed, for example, by executing executable commands stored in a non-transitory computer readable medium—for example, the memory 106—using processor 104 of the server computer 100.

The server computer 100 and the database 102 are implemented, for example, using an APACHE TOMCAT server computer and an open source PACS server named DCM4CHEE for developing the database access according to the query protocol of the database 102. A user of the client computer 110A, 110B is presented with a list of data files that are available on the database 102 of the PACS server, which is populated dynamically using, for example, Java Server Pages (JSP) and servlets on the "TOMCAT" server. For displaying the list, the server queries the tables in the "DCM4CHEE" database for a list of available data files and the location on disk—local or remote using a Network File System (NFS). For example, "DCM4CHEE" uses "postgres" as the back-end PACS database and the query uses Structured Query Language (SQL).

When the user clicks on a link to load a selected data file, the processor of the client computer sends a request using, for example, "HTTP GET". The server computer 100 uses a servlet that matches the GET parameters with the corresponding SQL query and then loads the data from the appropriate location on the disk.

Customization of the interface occurs between the servlet that queries the database and the front-end PACS server, i.e. the customization comprises the provision of a servlet that queries the PACS database using the appropriate database protocol—connection and schema. In the case of the "DCM4CHEE" database it is postgres and SQL and the "DCM4CHEE" schema. Some PACS databases use ORACLE® for which an ORACLE® interface—based on a Java servlet for querying the database and locating appropriate tables—is provided. Interfaces for other types of databases are provided in a similar fashion.

Preferably, the server computer 100 comprises an internal data loader. The data loader is built, for example, on a plug-in architecture that enables loading of a variety of data formats—including DICOM. The data loader parses the DICOM wrapper and loads the raw pixel data into memory. This process obviates re-writing of the source DICOM data files into another type of data file on disk—for example, in a data pre-processing step. Because DICOM is an open-standard it enables opening of data stored in any PACS database using the DICOM communications protocol.

The server computer 100 is preferably connected to the database 102 via a high bandwidth connection such as, for example, striped Ethernet, Fibrechannel or Infiniband. The separation of the DICOM communication from the high performance image data communication enables optimization of the high performance image data communication without impacting the DICOM communication or consuming resources of the hospital local area network.

The present invention has been described herein with regard to preferred embodiments. However, it will be obvious to persons skilled in the art that a number of variations and modifications can be made without departing from the scope of the invention as described herein.

What is claimed is:

1. A method for accessing a data file comprising:
   receiving at a server computer a request for accessing a data file of a plurality of data files stored in a database, the server computer being connected to the database via a first communication link and a separate second communication link;
   accessing, in the database, metadata associated with the data file via the first communication link using a first query protocol;
   locating, via the first communication link using the first query protocol, the data file in the database in dependence upon the metadata; and,
   accessing in the database at least a portion of data stored in the data file via the second communication link using a second query protocol and wherein the second query protocol is different from the first query protocol.

2. A method as defined in claim 1 wherein the first query protocol is a standard query protocol and wherein the metadata are transmitted according to a standard communication protocol associated with the first communication link.

3. A method as defined in claim 2 wherein the second query protocol is a high performance query protocol of the database and wherein the data are transmitted according to a high performance communication protocol associated with the second communication link, the second communication link being a high performance communication link.

4. A method as defined in claim 2 wherein the standard query protocol is a DICOM query protocol and wherein the metadata are transmitted according to a DICOM communication protocol associated with the first communication link.

5. A method as defined in claim 2 wherein the plurality of data files is stored in a PACS database.

6. A method as defined in claim 1 comprising:
   accessing in the database a table indicative of available data files via the first communication link using the first query protocol;
   generating a list of the available data files stored in the database in dependence upon the table;
   presenting the list to a user in a human comprehensible fashion; and,
   receiving data indicative of the data file to be accessed.

7. A method as defined in claim 6 comprising:
   using a servlet matching the data indicative of the data file to be accessed with a corresponding query according to the second query protocol.

8. A method as defined in claim 6 comprising:
   using the server computer processing the at least a portion of data stored in the data file and generating view data in dependence thereupon;
   transmitting the view data to a client computer connected to the server computer via a communication network;
   using the client computer displaying the view data in a human comprehensible fashion.

9. A method as defined in claim 1 comprising parsing the data file for accessing raw data.

10. A method as defined in claim 1 wherein a request is received for accessing a data file stored in a PACS database.

11. A method as defined in claim 1 wherein the metadata are accessed via a standard communication link and using a standard communication protocol and wherein the data file is accessed via a high performance link and using a high performance communication protocol.

12. A non-transitory computer readable medium having stored therein executable commands for execution on a processor of a server computer, the, server computer being connected to the database via a first communication link and a separate second communication link, the processor when executing the commands performing:
   accessing, in the database, metadata associated with the data file via the first communication link using a first query protocol;
   locating, via the first communication link using the first query protocol, the data file in the database in dependence upon the metadata; and,
   accessing in the database at least a portion of data stored in the data file via the second communication link using a second query protocol and wherein the second query protocol is different from the first query protocol.

13. A non-transitory computer readable medium as defined in claim 12, the storage medium having stored therein executable commands for execution on a processor of a server computer, the processor when executing the commands performing:
   accessing in the database a table indicative of available data files via the first communication link using the first query protocol;
   generating a list of the available data files stored in the database in dependence upon the table;
   presenting the list to a user in a human comprehensible fashion; and,
   receiving data indicative of the data file to be accessed.

14. A method for accessing a data file in a PACS database comprising:
   receiving at a server computer a request for accessing a data file of a plurality of data files stored in the PACS database, the server computer being connected to the PACS database via a standard communication link and a separate high performance communication link;
   accessing, in the PACS database, metadata associated with the data file via the standard communication link using a standard query protocol;
   locating, via the first communication link using the first query protocol, the data file in the PACS database in dependence upon the metadata; and, accessing in the PACS database at least a portion of data stored in the data file via the high performance communication link using a high performance query protocol.

15. A method as defined in claim 14 wherein the standard query protocol is a DICOM query protocol and the standard communication link is a DICOM communication link.

\* \* \* \* \*